(12) United States Patent
Hall et al.

(10) Patent No.: US 10,060,112 B1
(45) Date of Patent: Aug. 28, 2018

(54) TOILET SYSTEM FOR DETECTING TAGS IN PHARMACEUTICAL AND NUTRITIONAL PRODUCTS WHICH ARE EXCRETED IN SOLID WASTE

(71) Applicants: David R. Hall, Provo, UT (US); Steven J. M. Butala, Provo, UT (US); Dan Allen, Springville, UT (US); Andrew Nguyen, Provo, UT (US); Conrad Rosenbrock, Provo, UT (US); Ben Swenson, Lehi, UT (US); Daniel Hendricks, Provo, UT (US); Travis Niederhauser, Mapleton, UT (US); John Christensen, Bluffdale, UT (US); Joshua Larsen, Spanish Fork, UT (US); Joe Fox, Spanish Fork, UT (US)

(72) Inventors: David R. Hall, Provo, UT (US); Steven J. M. Butala, Provo, UT (US); Dan Allen, Springville, UT (US); Andrew Nguyen, Provo, UT (US); Conrad Rosenbrock, Provo, UT (US); Ben Swenson, Lehi, UT (US); Daniel Hendricks, Provo, UT (US); Travis Niederhauser, Mapleton, UT (US); John Christensen, Bluffdale, UT (US); Joshua Larsen, Spanish Fork, UT (US); Joe Fox, Spanish Fork, UT (US)

( * ) Notice: Subject to any disclaimer, the term of this patent is extended or adjusted under 35 U.S.C. 154(b) by 0 days.

(21) Appl. No.: 15/611,348

(22) Filed: Jun. 1, 2017

(51) Int. Cl.
| | | |
|---|---|---|
| *E03D 9/10* | (2006.01) | |
| *E03D 5/10* | (2006.01) | |
| *E03D 5/014* | (2006.01) | |
| *G01N 33/58* | (2006.01) | |
| *G01N 33/487* | (2006.01) | |
| *B01F 1/00* | (2006.01) | |
| *G01N 33/00* | (2006.01) | |

(52) U.S. Cl.
CPC ............... *E03D 9/10* (2013.01); *E03D 5/014* (2013.01); *E03D 5/10* (2013.01); *G01N 33/48785* (2013.01); *G01N 33/582* (2013.01); *B01F 1/0027* (2013.01); *G01N 2033/0003* (2013.01)

(58) Field of Classification Search
CPC .. E03D 5/10; E03D 5/014; E03D 9/10; G01N 33/48785; G01N 33/582
USPC .................................................. 4/320, 256.1
See application file for complete search history.

(56) References Cited

U.S. PATENT DOCUMENTS

| | | | | |
|---|---|---|---|---|
| 2009/0260143 A1* | 10/2009 | Storm | ....................... | E03D 9/10 4/319 |
| 2016/0122989 A1* | 5/2016 | Liu | ........................... | E03D 5/10 4/422 |

\* cited by examiner

*Primary Examiner* — Tuan N Nguyen

(57) ABSTRACT

We disclose a toilet system which analyzes solid waste to detect tags which were associated with pharmaceutical or nutritional products and excreted in the solid waste of a user. The toilet system may include a receptacle for receiving solid waste, a liquid dispenser for providing a liquid to assist in dispersing the solid waste, a solid waste dispersing system which may mix the solid waste with the liquid thereby homogenizing the solid waste, and an electromagnetic signature detector which may analyze the tags in the solid waste. The electromagnetic signature detector may include a selective binding surface which may bind tags present in the solid waste and which may be connected to a transducer which senses the presence of bound tags.

20 Claims, 5 Drawing Sheets

TOILET SYSTEM FOR DETECTING TAGS IN PHARMACEUTICAL AND NUTRITIONAL PRODUCTS WHICH ARE EXCRETED IN SOLID WASTE

BACKGROUND

Field of the Invention

This disclosure relates to methods of detecting tags in associated with pharmaceutical and nutritional products and for analyzing solid waste.

Background of the Invention

Detecting and verifying consumption of pharmaceutical or nutritional products is a challenge for managing product distribution, patient treatment, drug compliance in patients and clinical trial subjects, drug abuse, counterfeit products, and confirming food ingredients and sources. A variety of tags have been identified, many of which are detectable in urine, at least in part, because of ease in sample collection and analysis. However, tags that are absorbed into the bloodstream, filtered by the renal system, and excreted in the urine are likely to undergo metabolic change and to be excreted over time in multiple urination events. A tag which is not absorbed into the bloodstream but which remains in the gastrointestinal tract until it is excreted in the feces would be less likely to be altered by bodily processes. In addition, much of the tag may be excreted over a defined time period.

Methods of collecting, processing, and analyzing solid waste are available but comprise multiple steps. Sample collection is often inconvenient and uncomfortable for the user. However, an analysis system that occurs in a medical toilet would be simpler and more discrete for the user and less time may elapse between sample collection and analysis. A toilet system for easily and discretely measuring tags which are added to pharmaceutical or nutritional products for identification and tracking of the products and which are excreted in solid waste is needed.

BRIEF SUMMARY OF THE INVENTION

We disclose a toilet system for detecting tags which were associated with pharmaceutical or nutritional products and which were excreted in solid waste. The toilet system may include a receptacle for receiving solid waste which may be a toilet bowl. The toilet system may include a liquid dispenser which may dispense a liquid solvent into the receptacle for at least partially liquifying the solid waste. The solid waste and liquid solvent may then enter a solid waste dispersing system through a conduit using a variety of mechanisms which include a plunger, air jets, water jets, and water sprays. The solid waste dispersing system includes a mixing device which may use forced propulsion or active mixing to homogenize the solid waste. Foam and water may also be added to the liquid solvent during homogenization.

The sample may be transferred to an electromagnetic signature detector which is in fluid communication with the solid waste dispersing system. Tags which include magnetic or paramagnetic particles may be separated and concentrated using magnetic forces before or after the solid waste enters the electromagnetic signature detector.

The electromagnetic signature detector may include a nuclear magnetic resonance (NMR) spectrometer, a fluorescence detector, a magnetic resonator, a radio-frequency identification (RFID) transceiver, or a light absorption spectrometer. In some embodiments, the electromagnetic signature detector includes a selective binding surface. The selective binding surface may selectively bind the tags present in solid waste. Then a transducer may sense binding of a tag to the selective binding surface.

DETAILED DESCRIPTION OF THE INVENTION

Definitions

Figure 1A:
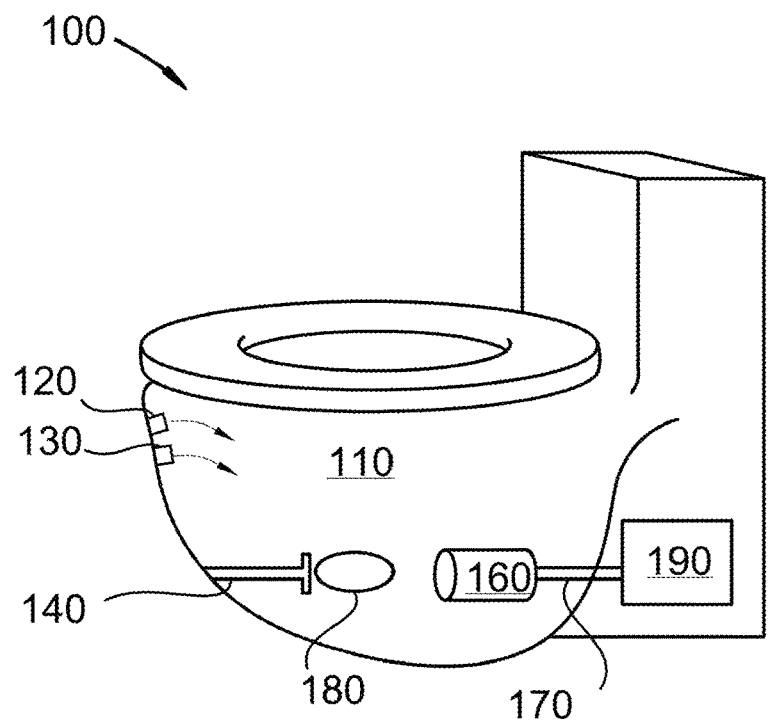
FIG. 1A illustrates a cross-sectional view of an embodiment of the disclosed toilet system in which a user has deposited solid waste.

Drug, as used herein, means any pharmacologically or physiologically active agent or mixture of agents. Drug may also include an active ingredient in a health product, including a nutritional supplement. Drug may include one or more placebos.

Pharmaceutical product, as used herein, means any product comprising a drug as defined herein.

Nutritional product, as used herein, means a nutritional supplement, food, food ingredient, or any product from which a user may derive nutrients.

User, as used herein, means a patient, a participant in a medical study, or any individual who has consumed a pharmaceutical or nutritional product which includes at least one tag as described herein. The user may be animal or human.

Medical toilet, as used herein, means a device that may be used to collect and analyze a biological sample, including solid waste, from a user. This may include a traditional water toilet. However, medical toilet, as used herein, may mean any device which may be used to collect and analyze biological samples according to the present disclosure.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a toilet system for detecting tagged pharmaceutical and nutritional products in solid waste, which may include feces. The toilet system may include a receptacle for receiving solid waste. In some embodiments, the receptacle is a toilet bowl. The toilet system may also include a liquid dispenser which may dispense a liquid solvent into the receptacle. In some embodiments, the liquid solvent is water. The liquid solvent may assist in dispersing, diluting, and partially or fully liquifying the solid waste.

The disclosed toilet system may further include a solid waste dispersing system. The solid waste dispersing system may include a mixing device for mixing the solid waste with the liquid solvent. A mechanical mixing device may provide forced propulsion of the solid waste and dispensed liquid into a static mixer. Some examples of static mixers which may be included in the mixing device are a helical static mixer and a plate-type static mixer.

The mechanical homogenizer may provide active mixing for instance, using one or more rotating blades. In some embodiments, the mixing device may include one or more of the following list: an air jet, a water jet, a water spray, and a mixing pump. Furthermore, the mixing device may include, but is not limited to, an ultrasound emitter, which may include a sonicator. In one example, the sonicator is a probe sonicator. In another example, the sonicator is a bath sonicator. In some embodiments, the solid waste dispersing system may include a combination of forced propulsion and active mixing. In some examples the solid waste dispersing system may include a piston which presses solid waste and liquid, foam, or a combination thereof against a rotating blade or rotating grate. In some examples, the propulsion is a result of water pressure. In some examples, the propulsion is a result of air pressure.

Some embodiments may include a foam dispenser. The foam dispenser may be in fluid communication with the solid waste dispersing system. The foam may include one or more surfactants or other chemicals which may assist in dispersing the solid waste.

Some embodiments may include a water dispensing conduit. The water dispensing conduit may be in fluid communication with the solid waste dispersing system. Water dispensed from the water dispensing conduit may further liquify and disperse the solid waste. In an example, the water dispensed from the water conduit may mix with the foam from the foam dispenser to help the foam to emulsify, mix, and/or disperse the solid waste.

A conduit may connect the receptacle with the solid waste dispersing system so that solid waste and liquid solvent may move from the receptacle into the solid waste dispersing system. In some embodiments, a plunger forces the solid waste from the receptacle, through the conduit, and into the solid waste dispersing system where the solid waste may be further mixed and dispersed. In other embodiments, air jets, water jets, or water sprays may move the solid waste from the receptacle, through the conduit, and into the solid waste dispersing system.

In some embodiments, the toilet system may further include a magnet. The magnet may be positioned adjacent to or within the solid waste dispersing system. The magnet may expose the contents of the solid waste dispersing system to a magnetic field. Consequently, the magnet may attract and thereby separate tags in the solid waste which include magnetic particles and/or paramagnetic particles.

In some embodiments, the magnet may be an electromagnet. In these embodiments, the current to the electromagnet may be actuated causing the magnetic or paramagnetic particles to be attracted to the magnetic field. The solid waste may move through and out of the solid waste dispersing system for analysis of non-magnetic tags. Then the electric current which actuated electromagnet may be terminated which also terminates the magnetic field. The magnetic or paramagnetic particles are then released and proceed through and out of the solid waste dispersing system for analysis.

The disclosed toilet system may further include an electromagnetic signature detector. The electromagnetic signature detector may be in fluid communication with the solid waste dispersing system. Consequently, the dispersed solid waste and/or isolated tags may move from the solid waste dispersing system into the electromagnetic signature detector for analysis of the tags.

In some embodiments, the electromagnetic signature detector includes a magnetic resonator. For example, the tags may include paramagnetic microparticles which are not absorbed into the bloodstream and, therefore, remain in the gastrointestinal tract. The paramagnetic microparticles may be excreted in solid waste which enters the disclosed toilet system. The paramagnetic microparticles may pass through the magnetic resonator, thus altering the permittivity and changing either the Q or resonant frequency of the magnetic resonator. To a good approximation, the magnetic resonator is not susceptible to changes in dielectric constant and, in any case, the solid waste is typically homogenized prior to entering the electromagnetic signature detector. Alternatively, the dielectric constant may be measured separately with a capacitive resonator and the dielectric constant compensated for. In an example, a magnetic field which is not homogeneous is applied to collect or concentrate the paramagnetic microparticles for measurement in a smaller magnetic resonator.

In some embodiments, the electromagnetic signature detector includes a radio-frequency identification (RFID) transceiver. For example, the tags may include RFID chips which are excreted in solid waste. The homogenized solid waste may pass near a high frequency (HF) or ultra high frequency (UHF) transceiver. The transceiver broadcast power may charge the passive chip which may modulate the transmit signal to encode its labeled RFD bit stream on the reflected signal.

In some embodiments, the electromagnetic signature detector includes a nuclear magnetic resonance (NMR) spectrometer. In an example, the tag may include an identifiable nuclear magnetic resonance signal. Examples of tags which have identifiable nuclear magnetic resonance signals are those which include an NMR-active isotope or which have NMR-active protons. Molecules with the unique electromagnetic or (equivalently) electromagnetically probable spin signature may be embedded in a host matrix. In some embodiments, the host matrix may be a clathrate or metal organic framework (MOF). The host matrix may be too large to be easily taken into the blood stream but the molecules, if not bound in the clathrate or MOF, would be absorbed into the bloodstream.

In some embodiments, the electromagnetic signature detector includes a fluorescent excitation source and a fluorescent signal detector. In an example, the tags include a fluorescent taggant. A pump light source may excite the fluorescent tag causing a fluorescent emission which the fluorescent detector measures.

In some embodiments, the tags are more detectable when liberated by dispersing them in a fluid medium. This allows the tags to be separated from other components of the solid waste and concentrated to provide a stronger signal in a smaller volume. Separation may be accomplished using magnetic forces. Separation may also be accomplished by taking advantage of differences in density using techniques which include centrifugation. Additionally, tags that include bound charges may be separated using ion chromatography.

In some embodiments, the electromagnetic signature detector comprises a gradient coil. The gradient coil may create a region that comprises a magnetic field gradient. The magnetic field gradient may draw magnetic or paramagnetic particles toward and into a sensing region in the electromagnetic signature detector. The sensing region may be within or include the analytical devices discussed above which may be part of the electromagnetic signature detector. In an example, the tags are paramagnetic microparticles coated with a fluorescent layer. The tags may be separated by a magnetic field gradient in a small detection zone then analyzed by measuring their fluorescent signature.

The electromagnetic signature detector may include a selective binding surface which may selectively bind tags present in the solid waste. The selective binding surface may include polynucleotides which are complementary to polynucleotides in tags, ligands which selectively interact with binding proteins on tags, binding proteins which selectively bind ligands on tags, and antibodies specific to molecules on tags. In some embodiments, the surface sensing technique includes surface plasmon resonance, surface acoustic wave, bulk acoustic wave, acoustic microresonator, or optical waveguide technology. In addition, the electromagnetic signature detector may include a transducer which may sense the binding of a tag to the selective binding surface. In some embodiments, the transducer measures radio frequency interference.

The electromagnetic signature detector may detect colorimetric signals. In examples, the tags may remain intact while passing through the gastrointestinal tract and be dissolved or broken up in response to ultrasound excitation (sonication) in the solid waste dispersing system or within the electromagnetic signature detector. The breakup of the particles may trigger a color change reaction upon exposure to reagent chemicals. In some embodiments, a chemical modifier of the tag, for example, a color change reagent, may be added to the tags within the electromagnetic signature detector and the color change measured.

Alternatively, the broken-up particles may emit additional fluorescent light when fluorophores inside the particles are exposed to light. Similarly, fluorophores associated with the tags may be quenched when the tags are broken up and the fluorophores quenched upon exposure to water.

In some examples the electromagnetic signature detector may modify the tags by heating the tags thus changing a detectable signal.

Figure 1B:
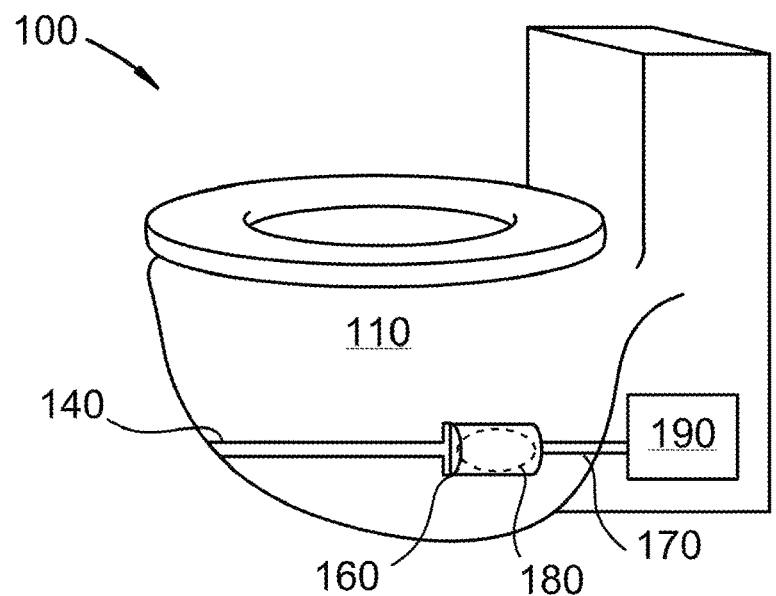
FIG. 1B illustrates toilet system of FIG. 1A in which a plunger has moved the solid waste into a solid waste dispersing system.

Referring now to the drawings, FIGS. 1A and 1B illustrate a cross-sectional view of medical toilet 100 which is an embodiment of the disclosed toilet system. Medical toilet 100 includes toilet bowl 110 which acts as a receptacle to receive solid waste 180 which may have been excreted by a user. Liquid dispenser 120 dispenses liquid, which may be water or other solvents, into toilet bowl 110. Foam dispenser 130 dispenses a foam product, which may include surfactants, into toilet bowl 110. The foam and the liquid solvent may assist in homogenizing and at least partially liquifying solid waste 180 as it is homogenized by solid waste dispersing system 160.

FIG. 1B illustrates medical toilet 100 as presented in FIG. 1A after solid waste 180 has entered solid waste dispersing system 160. Plunger 140 pushes solid waste 180, the solvent dispensed by liquid dispenser 120, and the foam dispensed by foam dispenser 130 into solid waste dispersing system 160. Solid waste dispersing system 160 may include a means for homogenizing and dispersing solid waste 180. After solid waste 180 has been processed by solid waste dispersing system 160, solid waste 180 moves through conduit 170 into electromagnetic signature detector 190. Electromagnetic signature detector 190 then analyzes solid waste 180 to detect tags which may be present therein.

Figure 2A:
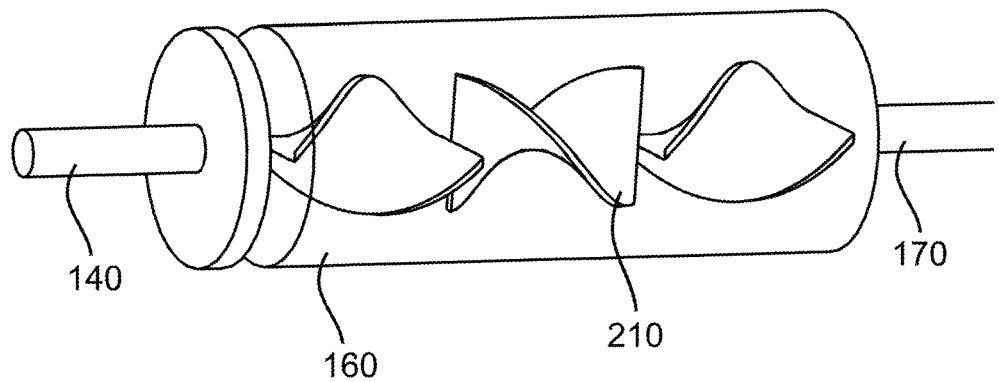
FIG. 2A illustrates cross-sectional view of a solid waste dispersing system according to an embodiment of the disclosure which includes a helical static mixer.
Figure 2B:
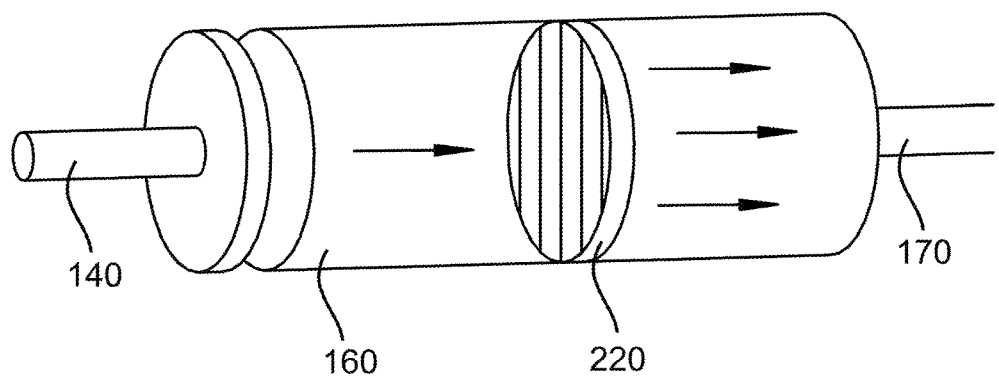
FIG. 2B illustrates cross-sectional view of a solid waste dispersing system according to an embodiment of the disclosure which includes a plate type static mixer.

FIGS. 2A and 2B illustrate cross-sectional views of two embodiments of solid waste dispersing system 160 which include static mixers for homogenizing and dispersing solid waste. FIG. 2A includes helical static mixer 210. Plunger 140 pushes the solid waste toward and through helical static mixer 210 to disperse and homogenize the solid waste. The process may also mix the solid waste with liquid solvents and foam. FIG. 2B includes plate type static mixer 220. Plunger 140 pushes solid waste through the multiple slits in plate type static mixer 210 which creates intense turbulence. The turbulence disperses and homogenizes the solid waste and may also mix the solid waste with liquid solvents and foam.

Figure 3:
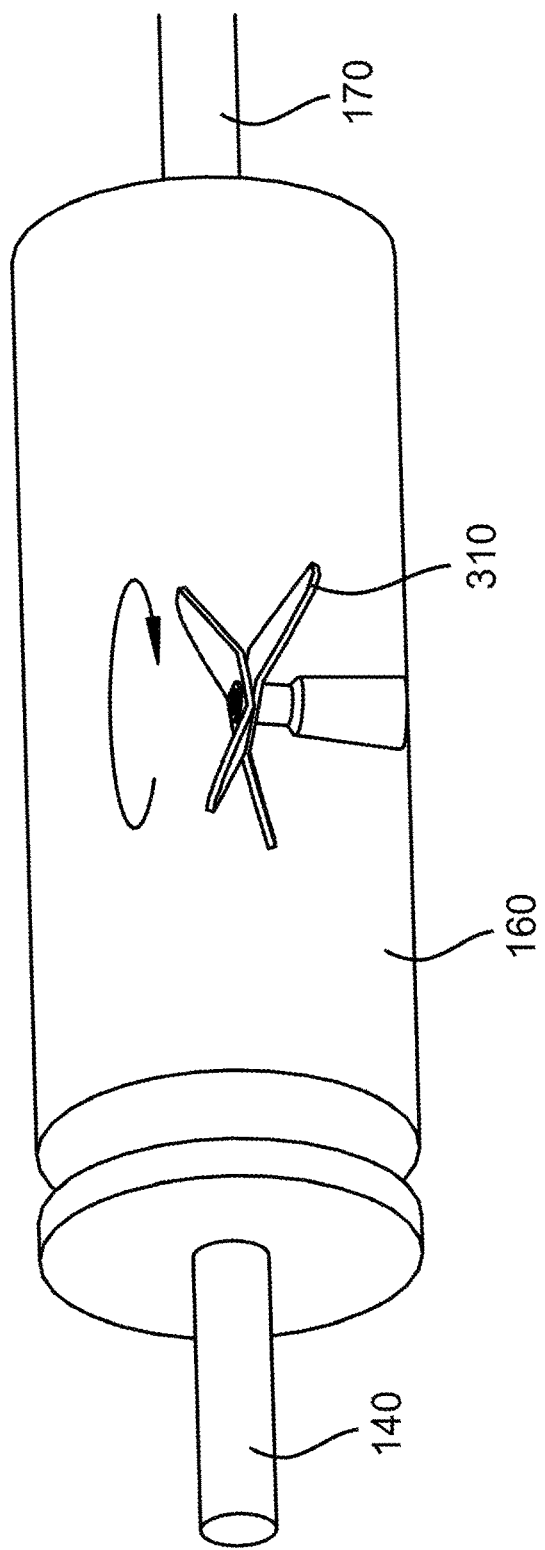
FIG. 3 illustrates cross-sectional view of a solid waste dispersing system according to an embodiment of the disclosure which includes a rotating blade.

FIG. 3 illustrates a cross-sectional view of an embodiment of solid waste dispersing system 160 which includes rotating blade 310. Rotating blade 310 may rotate as illustrated by the arrow. The blades of rotating blade 310 may chop and mix the solid waste causing it to be dispersed and homogenized. Rotating blade 310 may also mix the solid waste with liquid solvents and foam.

Figure 4:
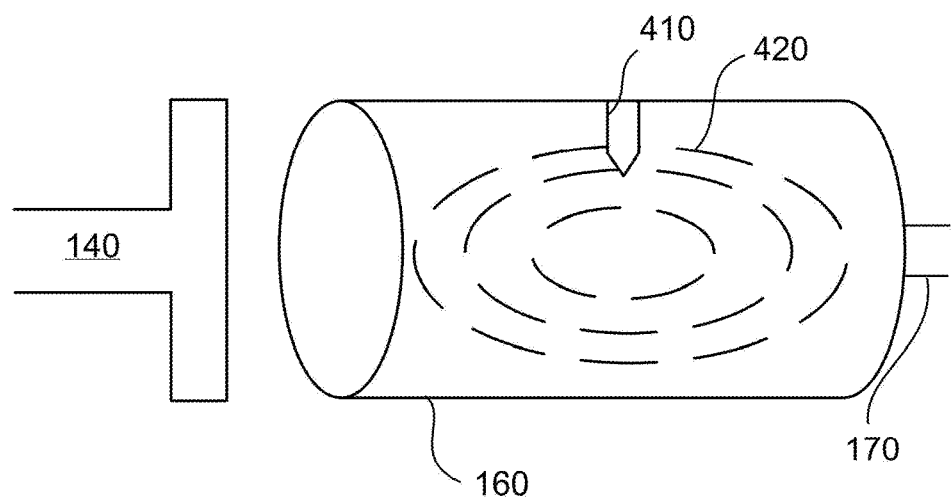
FIG. 4 illustrates cross-sectional view of a solid waste dispersing system according to an embodiment of the disclosure which includes a probe sonicator.

FIG. 4 illustrates a cross-sectional view of an embodiment of solid waste dispersing system 160 which includes sonicator probe 410. Upon actuation, sonicator probe 410 creates sonic waves 420 throughout the contents of solid waste dispersing system 160 which may include solid waste, and in some embodiments, the liquid solvent and foam. The sonic waves may agitate the contents of solid waste dispersing system 160 causing it to be dispersed and homogenized.

Figure 5:
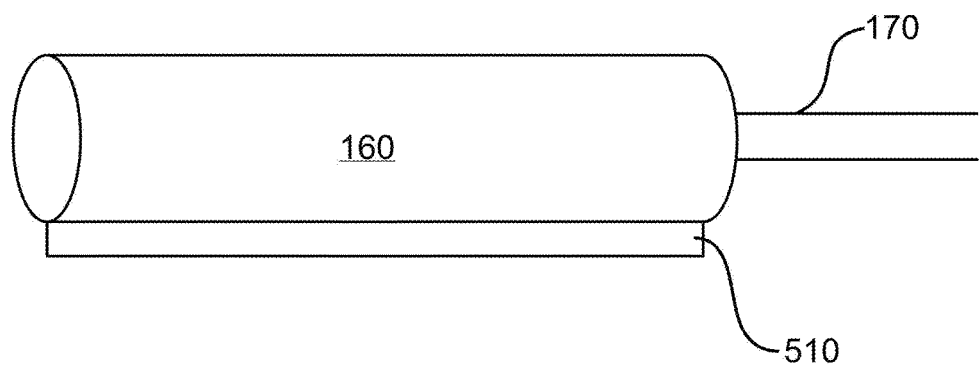
FIG. 5 illustrates cross-sectional view of a solid waste dispersing system according to an embodiment of the disclosure which includes a magnet which may collect paramagnetic tags.

FIG. 5 illustrates a cross-sectional view of an embodiment of solid waste dispersing system 160 which includes electromagnet 510. Electromagnet 510 may be present in embodiments of dispersing system 160 which include a variety of mechanisms for dispersing solid waste, including, but not limited, to those illustrated in FIGS. 2A, 2B, 3, and 4. When actuated, electromagnet 510 may attract tags which comprise magnetic or paramagnetic particles. The magnetic or paramagnetic particles may consequently be separated from the contents of solid waste dispersing system 160 during or after the solid waste is dispersed. Dispersed solid waste may proceed through conduit 170 into the electromagnetic signature detector where tags which do not include magnetic or paramagnetic particles may be analyzed. The electric current which actuated electromagnet 510 may then be terminated. The magnetic or paramagnetic particles may then be released from the magnetic field produced by electromagnet 510 and may continue through conduit 170 for analysis.

Figure 6:
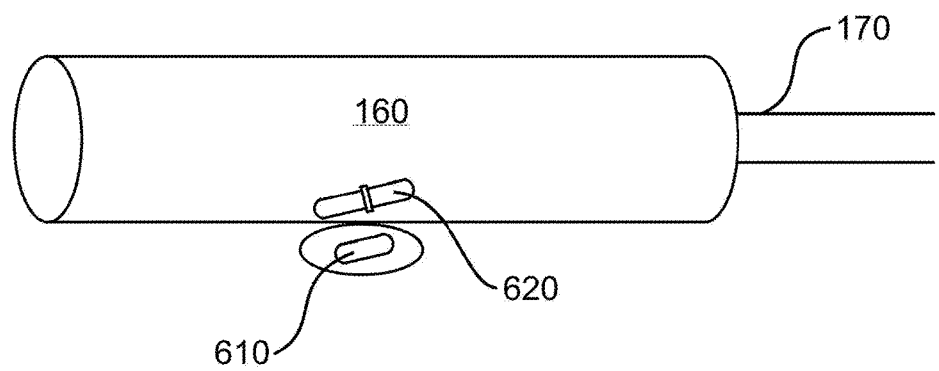
FIG. 6 illustrates cross-sectional view of a solid waste dispersing system according to an embodiment of the disclosure which includes a magnetic stir bar.

FIG. 6 illustrates a cross-sectional view of an embodiment of solid waste dispersing system 160 which includes magnetic stir bar 620. Rotating magnet 610 may rotate causing magnetic stir bar 620 to rotate. The rotation of magnetic stir bar 620 may mix the contents of solid waste dispersing system 160.

While specific embodiments have been described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A toilet system for detecting tagged pharmaceutical and nutritional products in solid waste comprising:
   a. a receptacle for receiving solid waste;
   b. a liquid dispenser, wherein the liquid dispenser dispenses liquid into the receptacle;
   c. a solid waste dispersing system, the solid waste dispersing system comprising:
      i. a mixing device; and
      ii. a conduit, wherein the solid waste dispersing system is in connection with the receptacle through the conduit;
   d. an electromagnetic signature detector, wherein the electromagnetic signature detector is in fluid communication with the solid waste dispersing system.

2. The toilet system of claim 1, further comprising a magnet, wherein the magnet is positioned adjacent to the solid waste dispersing system, and wherein the magnet exposes the contents of the solid waste dispersing system to a magnetic field.

3. The toilet system of claim 2, wherein the magnetic comprises an electromagnet.

4. The toilet system of claim 1, further comprising a foam dispenser, wherein the foam dispenser is in fluid communication with the solid waste dispersing system.

5. The toilet system of claim 1, wherein the mixing device comprises an ultrasound emitter.

6. The toilet system of claim 1, wherein the mixing device comprises a static mixer.

7. The toilet system of claim 6, wherein the static mixer consists of a helical static mixer or a plate type static mixer.

8. The toilet system of claim 1, wherein the mixing device comprises a water jet or water spray.

9. The toilet system of claim 1, wherein the mixing device comprises a rotating blade.

10. The toilet system of claim 1, wherein the mixing device comprises a mixing pump.

11. The toilet system of claim 1, further comprises a plunger, wherein the plunger forces solid waste from the receptacle into the solid waste dispersing system.

12. The toilet system of claim 1, further comprising at least one water dispensing conduit, wherein the at least one water dispensing conduit is in fluid communication with the solid waste dispersing system.

13. The toilet system of claim 1, wherein the electromagnetic signature detector comprises a magnetic resonator.

14. The toilet system of claim 1, wherein the electromagnetic signature detector comprises a gradient coil, wherein the gradient coil creates a region comprising a magnetic field gradient for drawing magnetic particles to a sensing region, and wherein the sensing region is within the electromagnetic signature detector.

15. The toilet system of claim 1, wherein the electromagnetic signature detector comprises a radio-frequency identification transceiver.

16. The toilet system of claim 1, wherein the electromagnetic signature detector comprises a nuclear magnetic resonance spectrometer.

17. The toilet system of claim 1, wherein the electromagnetic signature detector comprises:
   a. a fluorescent excitation source; and
   b. a fluorescent signal detector.

18. The toilet system of claim 1, wherein the electromagnetic signature detector further comprises:
   a. a selective binding surface, wherein the selective binding surface selectively binds tags present in solid waste; and
   b. a transducer, wherein the transducer senses binding of the tags to the selective binding surface.

19. The toilet system of claim 18, wherein the transducer measures radio frequency interference.

20. The toilet system of claim 1, wherein the mixing system comprises a homogenizer.

* * * * *